(12) United States Patent
Winkler et al.

(10) Patent No.: US 11,377,404 B2
(45) Date of Patent: Jul. 5, 2022

(54) PROCESS AND PLANT FOR PRODUCING ALPHA OLEFINS

(71) Applicant: LINDE GmbH, Pullach (DE)

(72) Inventors: Florian Winkler, Munich (DE); Richard Schneider, Uffing am Staffelsee (DE); Florian Mündl, Otterfing (DE)

(73) Assignee: LINDE GmbH, Pullach (DE)

(*) Notice: Subject to any disclaimer, the term of this patent is extended or adjusted under 35 U.S.C. 154(b) by 0 days.

(21) Appl. No.: 17/425,820

(22) PCT Filed: Jan. 28, 2020

(86) PCT No.: PCT/EP2020/051984
§ 371 (c)(1),
(2) Date: Jul. 26, 2021

(87) PCT Pub. No.: WO2020/157034
PCT Pub. Date: Aug. 6, 2020

(65) Prior Publication Data
US 2022/0162140 A1    May 26, 2022

(30) Foreign Application Priority Data

Jan. 28, 2019 (EP) .................... 19154007

(51) Int. Cl.
*C07C 7/17* (2006.01)
*C07C 7/148* (2006.01)
*C07C 2/08* (2006.01)

(52) U.S. Cl.
CPC .............. *C07C 7/17* (2013.01); *C07C 2/08* (2013.01); *C07C 7/1485* (2013.01)

(58) Field of Classification Search
CPC ............ C07C 7/17; C07C 2/08; C07C 7/1485
See application file for complete search history.

(56) References Cited

U.S. PATENT DOCUMENTS

| 3,367,987 A | 2/1968 | Walsh |
| 3,424,810 A | 1/1969 | Suatoni |

(Continued)

FOREIGN PATENT DOCUMENTS

| EP | 0648721 A1 | 4/1995 |
| EP | 3338884 A1 | 6/2018 |

(Continued)

OTHER PUBLICATIONS

PCT/EP2020/051984 International Preliminary Report on Patentability dated Feb. 2, 2021; 5 pages.

(Continued)

*Primary Examiner* — Thuan D Dang
(74) *Attorney, Agent, or Firm* — Lathrop GPM LLP

(57) ABSTRACT

A process (100) for the production of linear alpha-olefins is proposed, wherein ethylene is subjected to catalytic oligomerization (1) in a feed mixture to obtain a product mixture containing alpha-olefins with different chain length and side compounds. In a primary fractionation (2), a primary fraction is formed using at least part of the product mixture, and in a secondary fractionation (4), a secondary fraction is formed using at least part of the primary fraction. The primary fractionation (2) and the secondary fractionation (4) are carried out such that the primary fraction and the secondary fraction predominantly contain one of the alpha-olefins and are low in or free of other alpha-olefins, that the primary fraction contains one or more of the side compounds, and that the secondary fraction is depleted relative to the primary fraction in the one or more side compounds. In an intermediate step (3) between the primary fractionation (2) and the secondary fractionation (4), to which at least part of the primary fraction is subjected, the one or more side compounds are at least partly converted to one or more secondary compounds, and the one or more (Continued)

Figure 1:
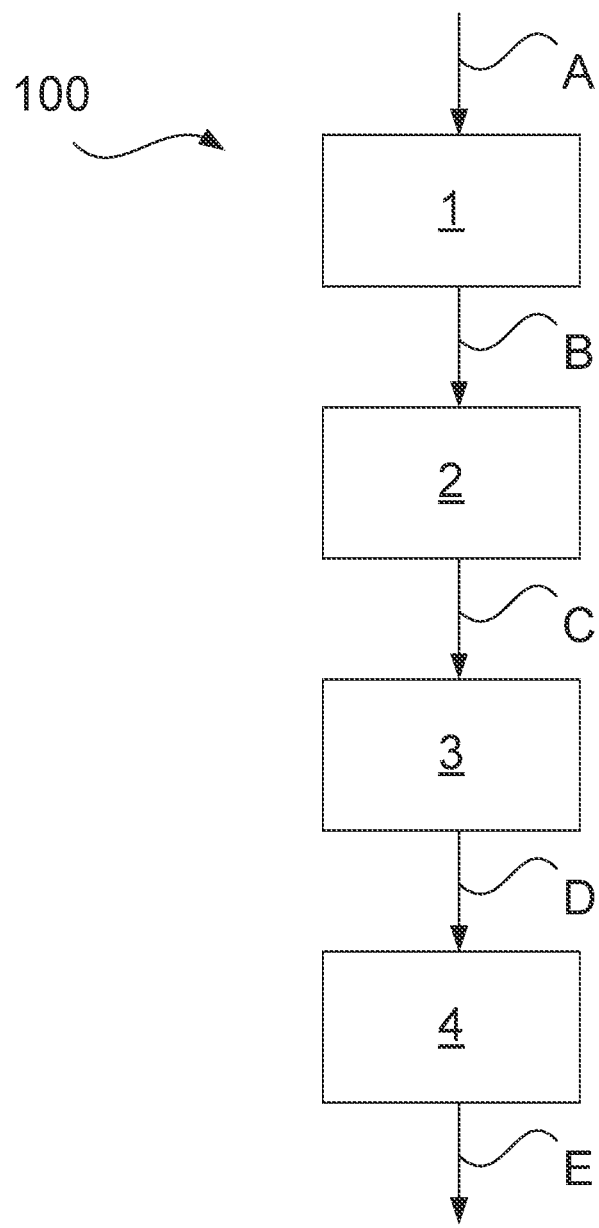

secondary compounds are at least partly separated in the secondary fractionation (4). The intermediate step (3) is carried out in such a way that not more than 0.8% of the alpha-olefin predominantly contained in the primary fraction or the part thereof subjected to the intermediate step is reacted. The intermediate step is carried out in the presence of 30 wt.-ppm to 200 wt.-ppm of water as reaction moderator and using a strongly acidic ion exchange resin.

13 Claims, 2 Drawing Sheets

(56) References Cited

U.S. PATENT DOCUMENTS

| | | |
|---|---|---|
| 4,511,753 A | 4/1985 | Smith et al. |
| 2003/0009070 A1* | 1/2003 | Doll ............... C07C 5/2518 585/666 |

FOREIGN PATENT DOCUMENTS

| | | |
|---|---|---|
| JP | H07149672 A | 6/1995 |
| RU | 2206557 C1 | 6/2003 |

OTHER PUBLICATIONS

PCT/EP2020/051984 International Search Report dated Mar. 31, 2020; 3 pages.

\* cited by examiner

PROCESS AND PLANT FOR PRODUCING ALPHA OLEFINS

The invention relates to a process for the preparation of an alpha-olefin and a corresponding plant according to the preambles of the independent claims.

PRIOR ART

The production of alpha-olefins (α-olefins) by oligomerization of ethylene is well known and described in the literature, for example in D. Steinborn, Fundamentals of Organometallic Catalysis, Wiley-VCH, 2012, especially chapter 8, "Oligomerization of Olefins". Important process variants are, for example, the Shell Higher Olefin Process (SHOP) and the Alpha-SABLIN process, as explained by Steinborn in subchapters 8.4.1 and 8.4.2 and elsewhere.

In the above processes, mixtures of even-numbered alpha-olefins are formed in a typical Schulz-Flory distribution, typically focusing on the formation of 1-butene and 1-hexene.

From EP 3 338 884 A1 a process for the oligomerization of ethylene to alpha-olefins is known, comprising an ethylene oligomerization step, a catalyst deactivation step and a product separation step, wherein the reactor is provided with a cooling circuit by means of which at least part of the reaction effluent is circulated through at least two interchangeable heat exchangers, said heat exchangers being alternately cleaned by an integrated cleaning device.

The problem described in JP H07-149672 A is to provide a process for producing 1-hexene on an industrial scale at low cost by the oligomerization of ethylene, followed by the separation of 1-hexene from the reaction solvent by distillation and recycling the reaction solvent to the reaction system. For solution, it is proposed to prepare 1-hexene by oligomerization of ethylene in a reaction solvent to obtain an alpha-olefin oligomer composition containing at least 50% by weight of 1-hexene. Separation of the 1-hexene and the reaction solvent from the reaction liquid containing the reaction solvent and the alpha-olefin oligomer composition is carried out by distillation, and the recovered reaction solvent is recycled to the reaction system.

According to U.S. Pat. No. 3,424,810 A, a mixture containing normal alpha-olefins and vinylidenes is treated with the acid form of a sulfonic acid cation exchange resin that has a macroreticular structure to obtain a resulting composition with greater amounts of normal alpha-olefin and fewer vinylidenes. The resulting composition is expected to be useful for alkylating aromatic compounds in the preparation of biodegradable detergents.

U.S. Pat. No. 3,367,987 A protected a process in which a mixture consisting essentially of hydrocarbons and containing predominantly at least one normal alpha-olefin having 6 to 8 carbon atoms and minor amounts of at least one vinylidene is contacted at a temperature between about −50° C. and about 100° C. with a Friedel-Crafts catalyst selected from the group consisting of ferric chloride, boron trifluoride and boron trifluoride etherate to selectively polymerize the vinylidene.

According to U.S. Pat. No. 4,511,753 A, vinylidene is selectively removed from an olefin mixture by reacting the mixture with either hydrogen sulfide or a hydrocarbyl mercaptan and then distilling the resulting mixture to obtain a substantially vinylidene-free product.

Medium chain length olefins containing as impurities 2-alkyl substituted isomers having a close boiling point are purified according to EP 0 648 721 A1 by (i) passing them over a solid acid catalyst under mild conditions to selectively isomerize the impurities at the double bond, and (ii) separating the isomerized olefins by distillation.

The oligomerization processes mentioned above, and in particular the Alpha-SABLIN process, are rather flexible in terms of product distribution. Thus, distributions with yields of, for example, 30 to 40 percent by weight of 1-butene and 1-hexene can be set. In this case, the fractions formed in each case usually meet the product quality requirements of the market with regard to foreign compounds.

On the other hand, when higher yields of, for example, 40 to 70 percent by weight of 1-butene and 1-hexene are set, the requirements of the market for the fractions are no longer met due to increased production of branched olefins in the individual fractions.

Nevertheless, correspondingly high yields are desired. Therefore, in such cases, a so-called superfractionation of the 1-butene, the 1-hexene, the 1-octene and/or the 1-decene fraction and a separation of branched olefins must be carried out in particular.

For example, depending on the distribution set, the 1-hexene fraction in the above cases may be contaminated with 0.5 to 2 percent by weight of the somewhat lower boiling component 2-ethyl-1-butene.

The 1-octene and 1-decene fractions are typically each contaminated by lower-boiling components that, however, boil very close to the respective alpha-olefins, namely 2-ethyl-1-hexene and 2-ethyl-1-octene.

Against this background, the present invention has the particular task of creating improved possibilities for the production of pure or specification-compliant alpha-olefin fractions.

DISCLOSURE OF THE INVENTION

Against this background, a process for the preparation of one of alpha-olefins and a corresponding plant according to the preambles of the independent claims are proposed. Embodiments are the subject of the dependent patent claims and the following description.

Before explaining the features of the invention, further principles of the invention will be explained and terms used will be defined.

Generally, as used herein, a "primary fractionation" of a mixture of alpha-olefins is understood to be the formation of a component mixture that contains a linear alpha-olefin of a particular carbon number but is low in or free of linear alpha-olefins of other carbon numbers. Such a component mixture is also referred to hereinafter as a "primary fraction" of a corresponding linear alpha-olefin, for example as a 1-butene, 1-hexene, 1-octene or 1-decene primary fraction. The characteristic linear alpha-olefin in each case, since it is contained in the predominant proportion, is also referred to below in each case as the "main component" in a corresponding primary fraction.

A corresponding primary fraction may contain lower boiling and/or higher boiling components in addition to the respective main component. This is the case in the process proposed according to the invention. By definition, however, these are not other linear alpha-olefins but, for example, branched olefins, paraffins or linear olefins with a non-terminal double bond. These each have a boiling point that is at a distance from a boiling point of the main component, this distance being less than a distance between the boiling point of the main component and a linear alpha-olefin that has two carbons more or less than the main component.

The lower and/or higher boiling components mentioned are separated in a so-called superfractionation, hereinafter also referred to as "secondary fractionation". The fractions formed in the secondary fractionation, hereinafter also referred to as "secondary fractions", are thus depleted of the lower boiling and/or higher boiling components compared with the corresponding primary fractions, but for technical reasons are typically not completely free of them. A 1-hexene secondary fraction typically contains no more than 0.5 weight percent, a 1-octene secondary fraction typically no more than 3 weight percent, and a 1-decene secondary fraction typically no more than 3.5 to 4 weight percent of heavier-boiling components. In a respective primary fraction, however, corresponding lighter and/or heavier boiling components may occur in significantly higher contents.

Superfractionation results in additional losses as well as increased operating costs and increased investment costs. This applies all the more the closer the boiling points of these lighter and/or heavier components are to those of the respective main component, since separation is made more difficult as a result. The 1-hexene fraction is particularly affected, because in this fraction the very close-boiling component 2-ethyl-1-butene corresponds to or exceeds the residual contents to be adjusted.

Advantages of the Invention

A process is known from RU 2 206 557 C1 in which 2-ethyl-1-butene in a component mixture is reacted with 1-hexene by selective isomerization of to 3-methyl-2-pentene over a catalyst. The catalyst is a macroporous sulfocationite with a volumetric capacity of 3.5 to 4.5 mg×equ. H$^+$/g. The process is carried out at a bed speed of 1 to 10 h$^{-1}$ and at a temperature of 40 to 80° C. The content of 2-ethyl-1-butene in the component mixture is more than 1 wt.-%, with 4.3 wt.-% mentioned in a specific example. The content of 1-hexene is more than 95 wt.-%. The 2-ethyl-1-butene contained is converted to 86 to 97%, with conversion losses of 1 to 2.6% of 1-hexene.

Whereas, under the conditions relevant in this connection, 1-hexene has a boiling point of 63 to 64° C. and 2-ethyl-1-butene a boiling point of 64 to 65° C., and these components are therefore very difficult or impossible to separate from one another, cis/trans-3-methyl-2-pentene has a boiling point of 67 to 72° C. and is therefore much easier to separate. A corresponding intermediate step therefore makes superfractionation or secondary fractionation much easier.

According to the invention, it has now been surprisingly recognized that such an intermediate step can also be carried out with a significantly lower conversion of 1-hexene or another alpha-olefin. In this way, a process can be created in which product losses are significantly reduced. The undesired conversion of 1-hexene is a side reaction in which cis/trans-2-hexene and/or cis/trans-3-hexene are formed.

In this regard, measures to reduce the undesirable reaction include the use of a reaction moderator, namely water, in the context of the present invention, while in an embodiment not according to the invention, the use of a less acidic catalyst is also contemplated, as explained below.

Overall, the invention proposes a process for the production of linear alpha-olefins in which ethylene in a feed mixture is subjected to catalytic oligomerization to obtain a product mixture containing alpha-olefins with different chain lengths and side compounds.

Within the scope of the present invention, basically all processes for the catalytic oligomerization of ethylene known in the prior art can be used. Reference is therefore made to the above explanations. In particular, the catalytic oligomerization can be carried out in the form of the known SABLIN process, as also explained at the outset. In particular, the catalytic oligomerization can be carried out with a yield of 40 to 70% by weight of 1-butene and 1-hexene.

Within the scope of the invention, in particular 1-butene, 1-hexene, 1-octene and/or 1-decene can be formed as linear alpha-olefins. In particular, the side compounds may be 2-ethyl-1-butene and 2-ethyl-1-hexene or, more generally, 2-ethyl-1-olefins having the same carbon number as the respective linear alpha-olefins formed as target products. Other side compounds possibly formed in a corresponding process include cis/trans-3-hexene, n-hexane, cis/trans-2-hexene, cis/trans-3-octene, cis/trans-4-octene, trans-2-octene, n-octane and cis-2-octene. The side compounds are not linear alpha-olefins.

In a primary fractionation, in the context of the present invention, a primary fraction is formed using at least part of the product mixture from the catalytic oligomerization, and in a secondary fractionation, a secondary fraction is formed using at least part of the primary fraction. For the terms primary fraction and secondary fraction or corresponding fractionation steps, reference is made to the explanations above. Secondary fractionation can be carried out in particular in the form of a known superfractionation. Primary and secondary fractionation can be carried out in particular in the form of thermal separation steps, in particular in the form of rectifications.

According to a particularly preferred embodiment of the present invention, the primary fraction may be dried before being subjected to secondary fractionation. All known processes can be used for drying, for example adsorptive drying using suitable adsorption materials. Since in the present invention a certain water content is used in the subsequent process step, because water is used as a reaction moderator, drying can also be carried out only downstream of this process step or can be omitted completely.

Within the scope of the present invention, the primary fractionation and the secondary fractionation are carried out in such a way that the primary fraction and the secondary fraction predominantly contain one of the linear alpha-olefins and are low in or free of other alpha-olefins, that the primary fraction contains one or more of the side compounds, and that the secondary fraction is depleted in the one or more side compounds compared to the primary fraction or (as far as technically reasonable and possible) free thereof. In other words, it is ensured in each case that, in addition to the respective main component in the form of the linear alpha-olefin, the primary fraction preferably does not contain any further linear alpha-olefins or contains them only to a very small extent.

Where reference is made herein to the formation of "one" primary fraction, this does not of course preclude the formation of further primary fractions with corresponding other linear alpha-olefins as the main component. For example, a 1-hexene primary fraction, a 1-octene primary fraction, a 1-decene primary fraction and/or a 1-dodecene primary fraction can be formed as primary fractions, each containing corresponding side compounds.

According to the invention, in an intermediate step between the primary fractionation and the secondary fractionation, to which at least part of the primary fraction is subjected, the one or more side compounds are at least partly converted to one or more secondary compounds, and the one or more secondary compounds are subsequently at least partly separated in the secondary fractionation.

As explained, 2-ethyl-1-butene in particular can be contained as a side compound in a 1-hexene primary fraction, which, as mentioned, differs only slightly from 1-hexene in its boiling point. By reaction in the intermediate step, cis/trans-3-methyl-2-pentene can be formed from this, which, with its higher boiling point, can be separated much more easily.

In a 1-octene primary fraction, for example, 2-ethyl-1-hexene may be present as a side compound. The boiling point of 1-octene is 121° C., that of 2-ethyl-1-hexene 120° C. By converting 2-ethyl-1-hexene to cis/trans-3-methyl-2-heptene with a boiling point of 122 to 126° C., the separation of this side compound is also facilitated. Because this side compound is shifted to the boiling position of other octene isomers by the aforementioned reaction, it can be separated together with them. Thus, 2-octene and 3-octene also boil above 122° C. The same applies to other side compounds in the same or comparable manner.

The invention is now characterized in that the intermediate step is carried out in such a way that not more than 0.8%, in particular not more than 0.5% or 0.2% based on weight, volume or molar basis of the alpha-olefin predominantly contained in the primary fraction or in the part thereof subjected to the intermediate step is reacted.

In particular, in the context of the present invention, the one or more side compounds may be reacted in the intermediate step down to a residual content of at most 0.4%, in particular at most 0.2% or 0.1% on a weight, mole or volume basis. This residual content may refer, for example, to a 2-ethyl-1-olefin having the same carbon number as the linear alpha-olefin predominantly contained in the primary and secondary fractions, and refers in particular to the content in the primary fraction after reaction in the intermediate step. The conversion of the 2-ethyl-1-olefin in the intermediate step may in particular be to a cis/trans-3-methyl-2-olefin again having the same carbon number.

In other words, within the scope of the present invention, advantageously, the 2-ethyl-olefin with the same carbon number is converted as completely as possible, i.e 2-ethyl-1-butene, 2-ethyl-1-hexene or ethyl-1-octene, depending on the fraction. In particular, the reaction is carried out to a residual content in the range already indicated above.

As mentioned, measures to reduce the undesired conversion of the respective linear alpha-olefin may herein include, in particular, the use of a reaction moderator, for example water, and/or the use of a less acidic catalyst as explained below.

In the process according to the invention, the intermediate step is carried out in the presence of water as reaction moderator. This applies in particular to a 1-hexene primary fraction. The water is used in the context of the present invention in a content of from 20 to 200 ppm by weight, in particular from 30 ppm by weight to 150 ppm by weight, from 60 ppm by weight to 130 ppm by weight or from 50 ppm by weight to 100 ppm by weight. Water may already be present in the product mixture subjected to primary fractionation or may be added separately. In particular, it is present in the reaction feed subjected to catalysis. By using water as a reaction moderator, the present invention has the particular advantage that the acid strength of the catalyst can be selectively reduced so that the undesired isomerization of the alpha olefin can thereby be greatly reduced. However, the desired isomerization of the target component is sufficiently preserved.

According to the invention, the process is carried out using a strongly acidic ion exchange resin in the intermediate step. In particular, a macroporous sulfocationite may be used as the strongly acidic ion exchange resin, for example a commercially available macroporous sulfocationite.

In the first embodiment of the present invention, the strongly acidic ion exchange resin can in particular have a volume-based capacity of at least 4 eq/kg, and/or the intermediate step can be carried out in this case at a bed speed of 5 to 40 $h^{-1}$ at temperatures of 30 to 60° C., in particular of 40 to 50° C. Under these reaction conditions, the advantages achievable by the use of the reaction moderator water according to the invention arise in a particular way.

In the present invention, a moderate conversion of, in particular, only 0.1 to 0.5 or 0.8% of the alpha-olefin predominantly contained in the primary fraction or its part subjected to the intermediate step is obtained at conversions of the side compound to be isomized of 85 to 95%. The process according to the present invention therefore considerably increases the yield compared to the prior art.

In an embodiment not according to the invention, the intermediate step could also be carried out using an alumina-based catalyst comprising, in particular, chi and gamma dialuminum trioxide. In this embodiment, the acid strength is already in a range where no moderator is required and thus a low conversion of the alpha-olefin is achieved compared to that of the 2-ethyl-1-olefin.

In particular, the alumina-based catalyst may have a surface area of 450 to 460 $m^2/g$ in this non-inventive embodiment of the present invention, and the intermediate step may be carried out here using a bed speed of 1 to 12 $h^{-1}$. Under these reaction conditions, the advantages of this embodiment not according to the present invention arise in a particular manner.

In the embodiment not according to the invention just explained, there is a particularly low conversion of, in particular, less than 0.1% of the alpha-olefin predominantly contained in the primary fraction or its part subjected to the intermediate step, with a conversion of the side compound to be isomized of 85 to 95%, and thus also an improved increase in yield.

In the context of the present invention, but also in the above-mentioned embodiment not according to the invention with a catalyst of lower acid strength, it has proved particularly advantageous to carry out the intermediate step at a temperature level of 60 to 100° C., in particular 70 to 90° C., and at a pressure level of 1.0 to 4.0 bar absolute pressure. In all embodiments of the present invention and in the embodiment not according to the present invention, regeneration of the catalyst used can furthermore be carried out, whereby, for example, several reactors can also be used in alternating operation, at least one of which is available for the intermediate step in each case.

In all cases, the present invention unfolds particular advantages if the product mixture contains as the main component(s) 1-hexene and/or 1-octene in a content of more than 50, 60, 70, 80 or 90% by weight.

Advantageously, the alpha-olefin which the primary fraction and the secondary fraction predominantly contain may be 1-hexene, the content of 1-hexene being more than 90% by weight. The side compound or one of the side compounds in such a case is in particular 2-ethyl-1-butene and/or the secondary compound or one of the secondary compounds in such a case is in particular 3-methyl-2-pentene.

However, the invention can also be used with particular advantage if the alpha-olefin which the primary fraction and the secondary fraction predominantly contain is 1-octene, the 1-octene content being more than 90% by weight. In such a case, the side compound or one of the side compounds is in particular 2-ethyl-1-hexene and/or the secondary compound or one of the secondary compounds is in such a case in particular 3-methyl-1-heptene.

The advantages of the explained embodiments, which include that a greater boiling point difference and thus a simplified separation are achieved by the implementation, have been explained in detail previously.

EXAMPLES

The process disclosed in the above-mentioned RU 2 206 557 C1 ("reference") was compared here with three examples ("Example 1" to "Example 3"). The results of this comparison as well as the catalysts used in each case and further reaction conditions are summarized in Table 1.

In the reference and in Examples 1 and 2, a macroporous sulfocationite was used as the catalyst, and in each of Examples 1 and 2, as in the reference, a commercially available product was used. Examples 1 and 2 differ from each other essentially in the amount of water used as reaction moderator, so that Example 2 can be used to demonstrate the advantages of one embodiment of the present invention.

In contrast, in Example 3, an amorphous chi and gamma dialuminum trioxide was used as the catalyst, again using a commercially available product. However, as in Example 1, a decidedly small amount of water was used. Example 3 thus demonstrates, merely for comparison with Examples 1 and 2, the features of the embodiment not according to the invention, which has been addressed several times.

reversible. By common methods of regeneration, the isomerization property can be fully restored to the initial activity. The frequency of regeneration can be avoided and/or reduced by using a pre-dryer upstream. In Example 4, a bed speed of 12 h$^{-1}$ was used at a temperature of 90° C., a pressure of 4 bar above atmospheric, with 3.8 g catalyst and with a moisture in the reaction feed of 40 wt.-ppm. The pre-dryer was run with 7 g Selexsorb CDX at about 20° C. The results are summarized in Table 2. In this table, columns 2 and 3 show the content of 2-ethyl-1-butene and 1-hexene in the reaction feed.

TABLE 2

| Time | Content 2-ethyl-1-butene | Content 1-hexene | Conversion 1-hexene | Conversion 2-ethyl-1-butene |
|---|---|---|---|---|
| 0 h | 1.0 wt.-% | 97.36 wt.-% | | |
| 2 h | 0.15 wt.-% | 97.33 wt.-% | <0,1% | 85% |
| 24 h | 0.28 wt.-% | 97.33 wt.-% | <0,1% | 72% |
| | | Regeneration | | |
| 30 h | 0.15 wt.-% | 97.32 wt.-% | <0,1% | 85% |
| | Installation pre-dryer (7g Selexsorb CDX) | | | |
| 32 h | 0.15 wt.-% | 97,32 | <0,1% | 85% |
| 56 h | 0.14 wt.-% | 97,29 | <0,1% | 86% |

In another example ("Example 5"), an amorphous chi- and gamma-dialuminum trioxide was likewise used as the catalyst, again using a commercially available product. Thus, the features of an embodiment not according to the invention are also shown here. It was shown that the losses

TABLE 1

| Parameter | Reference | Example 1 | Example 2 | Example 3 |
|---|---|---|---|---|
| Bed speed | 1-10 h$^{-1}$ | 30-90 h$^{-1}$ | 5-40 h$^{-1}$ | 1-10 h$^{-1}$ |
| Temperature | 40-80° C. | 40-60° C. | 40-60° C. | 60-90° C. |
| Absolute pressure | 1.0-3.0 bar | 1.0-4.0 bar | 1.0-4.0 bar | 1.0-4.0 bar |
| Catalyst | Amberlyst 15 | Lewatite K-2649 | Lewatite K-2649 | Selexsorb CDX |
| Type of catalyst | | macroporous sulfocationite | | amorphous chi and gamma dialuminum trioxide |
| Properties of catalyst | volume-related capacity 3.5-4.5 mg × equ. H$^+$/g | capacity by volume min. 4.7 eq/kg (dry) | | Surface 450-460 m$^2$/g |
| Alpha-olefin in reaction feed | 95 wt.-% | | 97 to 99 wt.-% | |
| 2-ethyl-1-butene in reaction feed | 4.3% wt.-% | | 1 to 1.5 wt.-% | |
| Water content | — | <20 wt.-ppm | <150 wt.-ppm | <20 wt.-ppm |
| Conversion alpha olefin | 1 to 2.6% | 0.5 to 2% | 0.1 to 0.5% | <0,1% |
| Conversion 2-ethyl-1-butene | 86 to 97% | | 85 to 95% | |

As can be seen from the comparison of the results, no appreciable improvements can be achieved in this regard with respect to the conversion of 1-hexene compared to the reference in Example 1, in which a comparable catalyst as in the reference and a small amount of water as reaction moderator were used. However, significant improvements occur when higher amounts of water are used according to Example 2, i.e. in the embodiment of the present invention, and when the chi and gamma dialuminum trioxide are used as catalyst according to Example 3, i.e. in the embodiment not according to the present invention.

In another example ("Example 4"), an amorphous chi- and gamma-dialuminum trioxide was likewise used as the catalyst, again using a commercially available product. Thus, the features of an embodiment not according to the invention are also shown here.

It has been shown that the deactivation of the catalyst is caused by the water content in the reaction feed and is also of 1-hexene can be minimized via the bed speed. A temperature of 90° C., a pressure of 4 bar above atmospheric, and 3.8 g catalyst were used. The humidity in the reaction feed was less than 20 wt.-ppm). The results are given in Table 3 below.

TABLE 3

| Bed speed | Content 2-ethyl-1-butene | Content 1-hexene | Conversion 1-hexene | Conversion 2-ethyl-1-butene |
|---|---|---|---|---|
| 0 h$^{-1}$ | 1.07 wt.-% | 97.90 wt.-%t | | |
| 3 h$^{-1}$ | 0.05 wt.-% | 97.82 wt.-% | 0,08% | 95% |
| 6 h$^{-1}$ | 0.07 wt.-% | 97.83 wt.-% | 0,07% | 93% |
| 12 hw | 0.19 wt.-% | 97.88 wt.-% | 0,02% | 82% |

DRAWINGS

In FIG. 1, a process for the preparation of linear alpha-olefins according to one embodiment of the invention is shown in the form of a schematic flow chart and designated 100 in total.

In the process 100, ethylene in a feed mixture A is subjected to catalytic oligomerization 1 to obtain a product mixture B containing alpha-olefins with different chain length and side compounds.

In a primary fractionation 2, a primary fraction C is formed using at least a part of the product mixture B, and in a secondary fractionation 4, a secondary fraction is formed using at least a part of the primary fraction C.

Primary fractionation 2 and secondary fractionation 4 are carried out such that the primary fraction and the secondary fraction predominantly contain one of the alpha-olefins and are low in or free of other alpha-olefins, that the primary fraction contains one or more of the side compounds, and that the secondary fraction is depleted relative to the primary fraction in the one or more side compounds.

In an intermediate step 3 between the primary fractionation 2 and the secondary fractionation 4, to which at least part of the primary fraction C is subjected, the one or more side compounds are at least partly converted to one or more secondary compounds.

The one or more secondary compounds formed in the intermediate step 3 are at least partially separated in the secondary fractionation 4. The intermediate step 3 is carried out in such a way that no more than 0.8% of the alpha-olefin predominantly contained in the primary fraction or the part thereof subjected to the intermediate step is converted.

Figure 2:
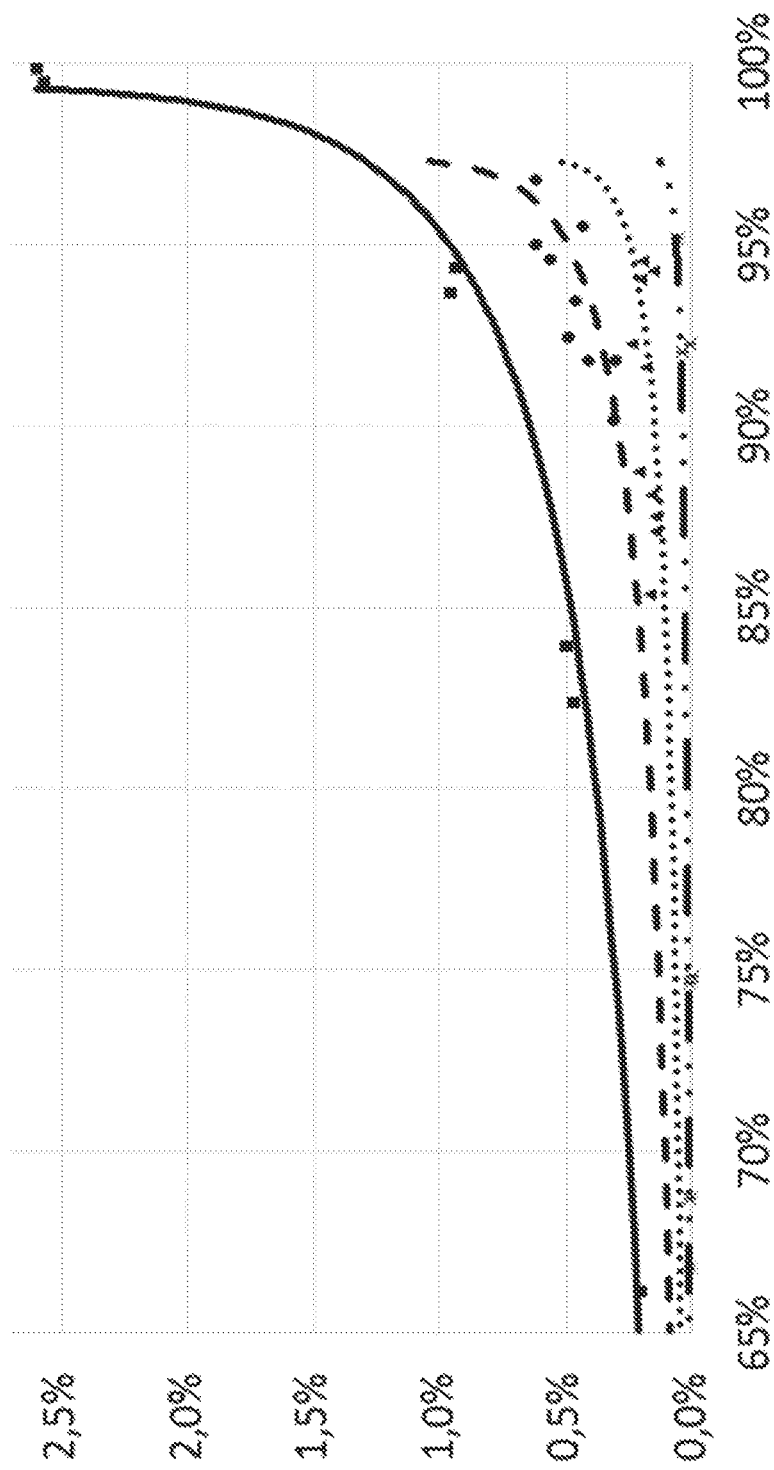

FIG. 2 shows the results of a series of experiments carried out with Lewatit K-2649 as catalyst (i.e., as in examples 2 and 3 above, a macroporous sulfocationite) and with different amounts of water in use as moderator, so that the advantages of one embodiment of the present invention are demonstrated here. In the diagram of FIG. 2, the (desired) conversion of 2-ethyl-1-butene is shown on the abscissa and the (undesired) conversion of 1-hexene is shown on the ordinate, each in percent.

The solid line with square data points illustrates the values obtained without water. The dashed line with round data points illustrates the values obtained with a water quantity of 60 wt.-ppm. The dotted line with triangular data points illustrates the values obtained with a water quantity of 100 wt.-ppm. The dash-dotted line with star-shaped data points illustrates the values obtained at a water volume of 130 ppm by weight.

From the values illustrated in FIG. 2 it is clear that a purely dry application leads to high losses of 1-hexene. An application with about 100 to 130 ppm by weight of water at the reactor outlet, as may result in one embodiment of the present invention, leads to considerable improvements with respect to these losses.

The invention claimed is:

1. A process (100) for the preparation of linear alpha-olefins, wherein
ethylene in a feed mixture is subjected to catalytic oligomerization (1) to obtain a product mixture containing alpha-olefins with different chain lengths and side compounds,
a primary fraction is formed in a primary fractionation (2) using at least part of the product mixture, and a secondary fraction is formed in a secondary fractionation (4) using at least part of the primary fraction,
the primary fractionation (2) and the secondary fractionation (4) are carried out such that the primary fraction and the secondary fraction predominantly contain one of the alpha-olefins and are low in or free of other alpha-olefins, the primary fraction contains one or more of the side compounds, and the secondary fraction is depleted in or free of the one or more side compounds relative to the primary fraction, and
in an intermediate step (3) between the primary fractionation and the secondary fractionation, to which at least part of the primary fraction is subjected, the one or more side compounds are at least partly converted to one or more secondary compounds and the one or more secondary compounds are at least partly separated in the secondary fractionation,
wherein the alpha-olefin which the primary fraction and the secondary fraction predominantly contain is 1-hexene, the side compound or one of the side compounds is 2-ethyl-1-butene, and the secondary compound or one of the secondary compounds is 3-methyl-2-pentene, or wherein the alpha-olefin which the primary fraction and the secondary fraction predominantly contain is 1-octene, the side compound or one of the side compounds is 2-ethyl-1-hexene, and the secondary compound or one of the secondary compounds is 3-methyl-1-heptene,
characterized in that
the intermediate step is carried out in the presence of 20 wt.-ppm to 200 wt.-ppm water as reaction moderator and using a strongly acidic ion exchange resin, so that not more than 0.8% of the alpha-olefin predominantly contained in the primary fraction or the part thereof subjected to the intermediate step is reacted.

2. The process of claim 1, wherein a macroporous sulfocationite is used as the strongly acidic ion exchange resin.

3. The process according to claim 1, wherein the strongly acidic ion exchange resin has a volume based capacity of at least 4 eq/kg.

4. The process according to claim 1, in which the intermediate step is carried out at a bed speed of 5 to 40 $h^{-1}$.

5. The process according to claim 1, wherein 0.1 to 0.8% of the alpha-olefin predominantly contained in the primary fraction or its part subjected to the intermediate step is reacted.

6. The process according to claim 1, in which the intermediate step is carried out at a temperature level of 60° C. to 100° C. and/or is carried out at a pressure level of 1.0 to 4.0 bar absolute pressure.

7. The process according to claim 1, wherein the product mixture contains the 1-hexene and/or the 1-octene in a content of more than 50, 60, 70, 80 or 90% by weight.

8. The process according to claim 1, wherein the alpha-olefin that the primary fraction and the secondary fraction predominantly contain is 1-hexene, wherein the content of 1-hexene is more than 90 wt.-%.

9. The process according to claim 1, wherein the alpha-olefin that the primary fraction and the secondary fraction predominantly contain is 1-octene, wherein the content of 1-octene is more than 90 wt.-%.

10. The process according to claim 7, wherein the product mixture contains the 1-hexene and/or the 1-octene in a content of more than 60% by weight.

11. The process according to claim 7, wherein the product mixture contains the 1-hexene and/or the 1-octene in a content of more than 70% by weight.

12. The process according to claim 7, wherein the product mixture contains the 1-hexene and/or the 1-octene in a content of more than 80% by weight.

13. The process according to claim 7, wherein the product mixture contains the 1-hexene and/or the 1-octene in a content of more than 90% by weight.

* * * * *